United States Patent
Greenwald et al.

[11] Patent Number: 6,013,283
[45] Date of Patent: Jan. 11, 2000

[54] ALKYL OR OLEFINIC ENDCAPPED POLYALKYLENE OXIDE SOLUBILIZER

[75] Inventors: Richard B. Greenwald, Somerset; Robert G. L. Shorr, Edison; Mike Alan Clark, Denville; Alahari Arunakumari, Belle Mead, all of N.J.

[73] Assignee: Enzon Inc., Piscataway, N.J.

[21] Appl. No.: 08/897,180

[22] Filed: Jul. 21, 1997

Related U.S. Application Data

[60] Division of application No. 08/459,057, Jun. 2, 1995, Pat. No. 5,686,110, which is a continuation-in-part of application No. 08/252,854, Jun. 2, 1994, abandoned.

[51] Int. Cl.[7] .............................. A61K 47/34; C08G 65/32
[52] U.S. Cl. .................. 424/486; 514/772.3; 525/403
[58] Field of Search ................ 424/486; 514/772.3; 525/403; 528/421

[56] References Cited

U.S. PATENT DOCUMENTS

| | | | |
|---|---|---|---|
| 2,898,267 | 8/1959 | Lindner | 167/42 |
| 4,215,116 | 7/1980 | Lover et al. | 424/217 |
| 4,511,563 | 4/1985 | Schmolka | 514/162 |
| 4,534,899 | 8/1985 | Sears | 260/403 |
| 4,904,466 | 2/1990 | Carson et al. | 424/76.3 |
| 4,960,790 | 10/1990 | Stella et al. | 514/449 |
| 5,030,448 | 7/1991 | Hunter | 424/83 |
| 5,160,734 | 11/1992 | Ganesan et al. | 424/78.38 |
| 5,283,317 | 2/1994 | Saifer et al. | 528/405 |
| 5,306,506 | 4/1994 | Zema et al. | 424/466 |
| 5,449,513 | 9/1995 | Yokoyama et al. | |
| 5,681,812 | 10/1997 | Coon et al. | |

FOREIGN PATENT DOCUMENTS

| | | | |
|---|---|---|---|
| 0118316 | 9/1984 | European Pat. Off. | C07F 9/10 |
| 0522937 | 1/1993 | European Pat. Off. | A61K 47/10 |

OTHER PUBLICATIONS

Forster, et al. J. Pharm. Pharmacol. 1988, 40: 325–328.
Boulard, J. pp. 214–234 of Candida Albicans: *Cellular and Molecular Biology*, R. Prasad, Editor, Springer–Verlag NY (1991).

*Primary Examiner*—Edward J. Webman
*Attorney, Agent, or Firm*—Roberts & Mercanti, LLP

[57] ABSTRACT

A method for rendering water-insoluble materials water-soluble is provided. The method is useful for solubilizing substantially water-insoluble bioactive materials such as drugs. This is accomplished by forming a non-covalently bonded complex between the drug and a polymer which is soluble in both water and an organic solvent. This is carried out by combining the desired medicinal agent with the polymer is an organic solvent, removing the solvent and dissolving the complex in water or aqueous buffer. When the organic solvent is evaporated, a solid complex is recovered which is water-soluble. Methods of treatment with the complexes are also provided.

11 Claims, 2 Drawing Sheets

ALKYL OR OLEFINIC ENDCAPPED POLYALKYLENE OXIDE SOLUBILIZER

This application is a divisional of U.S. patent application Ser. No. 08/459,057, filed Jun. 2, 1995, now U.S. Pat. No. 5,686,110, which is a continuation-in-part of U.S. patent application Ser. No. 08/252,854 filed Jun. 2, 1994, now abandoned.

BACKGROUND OF THE INVENTION

1. Field of the Invention

The present invention relates to a method for rendering water-insoluble materials water-soluble. More particularly, the invention pertains to a method for making substantially water-insoluble bioactive materials, such as drugs, more water-soluble by forming non-covalent complexes with polymers which are soluble in both water and organic solvents.

2. Description of the Prior Art

It is known in the art that a wide variety of bioactive materials are either completely or substantially insoluble in water. It would be most advantageous if such materials could be made more water-soluble while maintaining their bioactive. In the prior art, when a promising drug candidate was found to be insufficiently water-soluble, research focussed on molecular alteration of the compound to produce a water-soluble analog, such as its salt form. However, many times such is not possible and a compound which has beneficial properties must be abandoned.

Other attempts at solubilizing drugs include, for example, U.S. Pat. No. 5,160,734 which discloses complexing a poorly water-soluble drug with a polyoxypropylene-polyoxyethylene block copolymer. A complex is formed by blending the polymer, drug and ethanol followed by granulation with lactose and vacuum drying. U.S. Pat. No. 5,030,448 suggests taking advantage of the hydroplhilic-hydrophobic portions of a polymer which is surface active. This system requires a hydrophobic central moiety instead of one which is water-soluble. U.S. Pat. No. 2,898,267 shows the use of polyalkylene oxide adducts of $C_9$–$C_{22}$ alkyl alcohols to form emulsions. U.S. Pat. No. 4,904,466 shows polymers which form gels at low water concentrations by using a $C_8$–$C_{20}$ group containing polyethylene ether surfactants in capped polyether polymer gels for drug delivery. U.S. Pat. No. 4,511,563 discloses analgesic gels using block copolymers of ethylene oxide and propylene oxide. Only mixtures are shown. None of these suggest a mechanism for making a water-insoluble component water-soluble.

SUMMARY OF THE INVENTION

The invention provides a water-soluble, polymeric compound having the structure:

R—X—Z—X—R'     (I)

wherein:

R is a $C_6$–$C_{30}$ alkyl, cycloalkyl, bicycloalkyl or olefin group;

X is independently selected from the group consisting of: oxygen, sulfur,

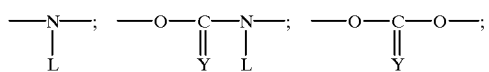

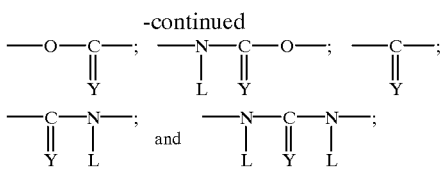

wherein L is H or a $C_{1-4}$ alkyl; and Y is O or S;

Z is a water-soluble polymer residue; and

R' is H, OH or $C_{1-24}$ alkyl.

The invention also provides a water-soluble complex comprising a substantially water-insoluble compound non-covalently bonded to one of the above-described polymeric compounds and methods of producing the complexes.

The invention still further provides a method of preparing solutions containing the above-described complexes. The method includes contacting a substantially water-insoluble compound with a polymeric compound of the structure shown above in the presence of an organic solvent; separating the complex from the organic solvent; and combining the complex with water.

In another aspect of the invention, there is provided water-soluble complexes of the polymer derivative described above along with a medicinal agent selected from the group consisting of Amphotericin-B and tacrine.

Yet another aspect of the invention includes methods of treatment. In this aspect of the invention, complexes described above containing a medicinal agent are administered to a mammal in need of the medicinal agent. Such treatment methods are preferably carried out by administering the complexes as part of an aqueous solution.

As a result of the present invention, the artisan is presented with an additional means of solubilizing substantially water-insoluble materials such as medicinal agents. In certain aspects of the invention, the polymeric complexes also allow a medicinal agent such as Amphotericin-B to be delivered in a manner which is substantially safer than methods previously used without loss of potency.

DETAILED DESCRIPTION OF THE PREFERRED EMBODIMENT

Figure 1:
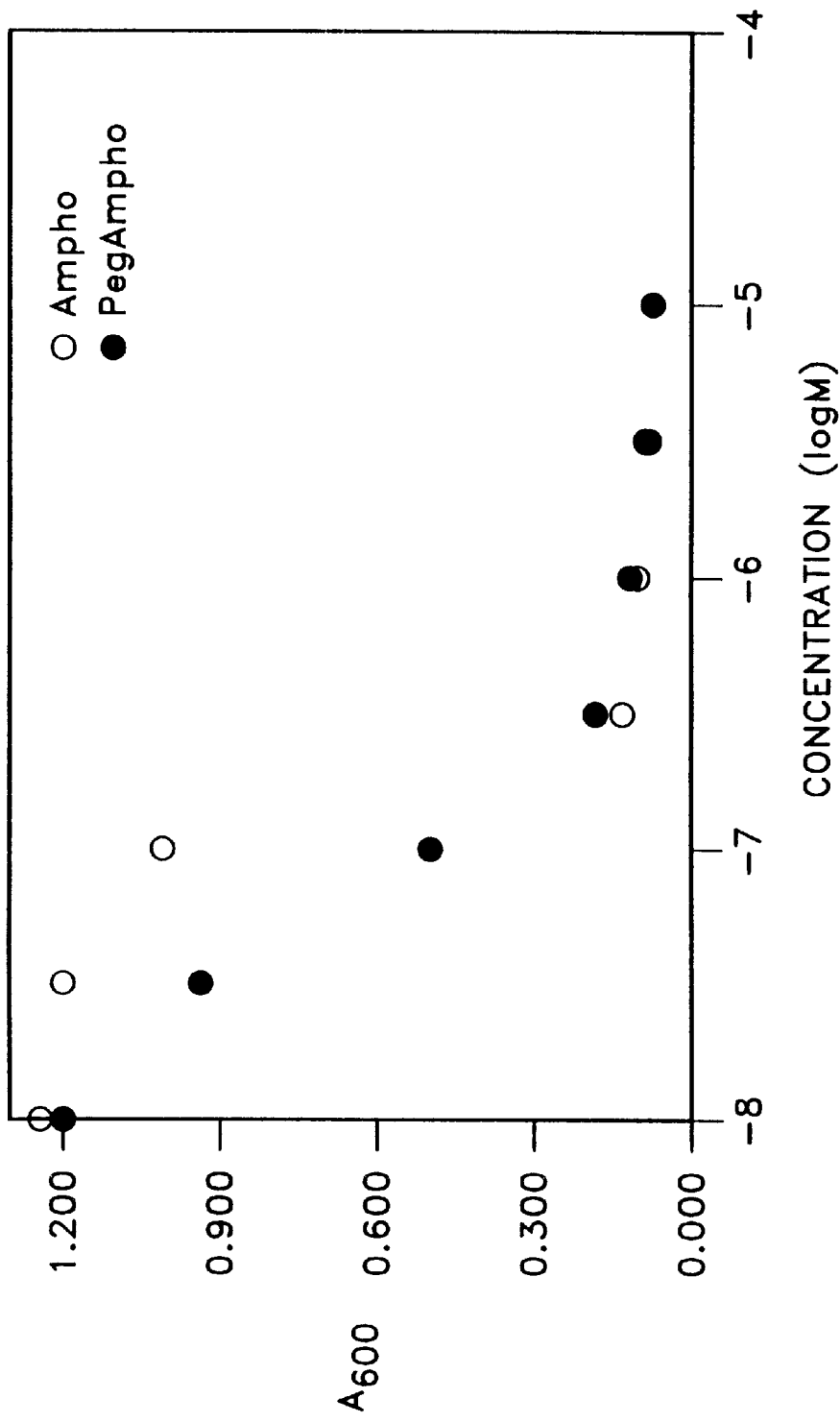
FIG. 1 is a graphical representation of the antifungal effect of amphotericin and polyethylene glycol conjugated amphotericin in accordance with the present invention on candida growth.

The invention provides methods for solubilizing substantially water-insoluble compounds such as medicinal agents. The methods include forming a complex of the water-insoluble compound and a water-soluble polymer in an approximately equimolar ratio. The polymer portion of the complex contains a terminal hydrophobic aromatic, alkyl or olefinic group which is believed to be in a non-covalent mating relationship with the water-insoluble compound.

The complex is formed by mixing the desired water-insoluble compound with the polymer in a suitable organic solvent such as ethanol, methanol, tetrahydrofuran, dimethylformamide, methylene chloride and mixtures thereof, removing the solvent and dissolving the residue in water or suitable aqueous buffer.

Molar ratios of polymer to target water-insoluble medicinal agent or drug range from about 1:1 to about 4:1. The amount of polymer to effect this result varies in proportion, molecular weight and chain length for each medicinal and can also be determined empirically.

The resultant compound may have a different HPLC spectrum from the water-insoluble compound, i.e., drug and polymer as individual components, but the same NMR spectra as a mixture of the two individual components. Nevertheless, no covalent bond is formed. When the complex is dissolved in an organic solvent, such as ethanol, the original components can be recovered. While Applicants are not bound by theory, it is believed that the hydrophobic portion of the water-insoluble polymer attracts the water-insoluble drug by Van Der Waals forces. Further, it is believed that the polymeric compounds do not act as surfactants to achieve the solubilizing effect. Surfactants are typically low molecular weight compounds (MW<1,000) used in severalfold molar excesses to form micelles. The polymeric compounds of the present invention, on the other hand, are of higher molecular weights ranging from about 1,000 to about 40,000. Furthermore, the polymeric compounds are preferably used in approximately equimolar ratios with the compound to be solubilized.

The polymeric compositions have the structure:

R—X—Z—X—R'  (I)

wherein R is a $C_6$–$C_{30}$ alkyl, cycloalkyl such as cyclooctyls, cyclodecyls and cyclododecyls; bicycloalkyl such as norbornyl derivatives and di-, tri- and sesquiterpenes; or an olefin group such as an oleic derivative.

Preferably, R is a $C_6$–$C_{24}$ alkyl group and, most preferably. R is a $C_8$–$C_{18}$ alkyl group. It is to be understood that suitable alkyls include straight and branched alkyls.

In alternative aspects of the invention, R is an aromatic group such as a phenyl, substituted phenyl, substituted phenyl and the like, or even a cyano-substituted group.

Each X is independently selected from the group consisting of:

oxygen, sulfur,

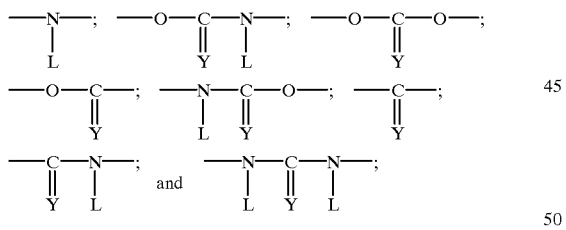

wherein L is H or a $C_{1-4}$ alkyl; and Y is O or S; and
R' is H, OH or $C_{1-24}$ alkyl. Preferably, R' is a $C_{1-4}$ alkyl group and most preferably $CH_3$.

The polymeric compounds are formed by capping a water-soluble polymer residue, designated Z herein, with XR or XR' groups. Mono-activated, alkyl-terminated polyalkylene oxides such as monomethyl-terminated polyethylene glycols (mPEG's) are preferred; bis-activated polyethylene oxides are also contemplated. Non-limiting examples of such water-soluble polymers include polyalkylene oxide homopolymers such as polyethylene glycol (PEG), polyoxyethylenated polyols, copolymers and block copolymers of PEG, PPG (polypropylene glycol) and/or EO (ethylene oxide), provided that the water solubility of a copolymer is maintained. Although polyethylene glycols vary substantially by weight, water-soluble polymer residues Z are formed from polymers having a molecular weight ranges of from about 1,000 to about 40,000 are usually selected for the purposes of the present invention. Molecular weights of from about 1,000 to about 7,500 are preferred and 2,000 to about 5,000 are particularly preferred. The polymer residues included herein are water-soluble at room temperature.

The polymeric compounds, therefore, have a molecular weight of from about 1,000 to about 40,000, more preferably from about 2,000 to about 12,000 and most preferably from about 2,000 to about 5,000. For purposes of the present invention, effectively non-antigenic means and all polymeric materials understood in the an as being substantially non-toxic and not eliciting an appreciable immunogenic response in mammals.

Synthesis of the water-soluble polymeric compounds of the present invention includes reacting equimolar amounts of an alkylated polyethylene glycol with a fatty alcohol or fatty amine in an inert solvent. The following are suitable reaction mechanisms:

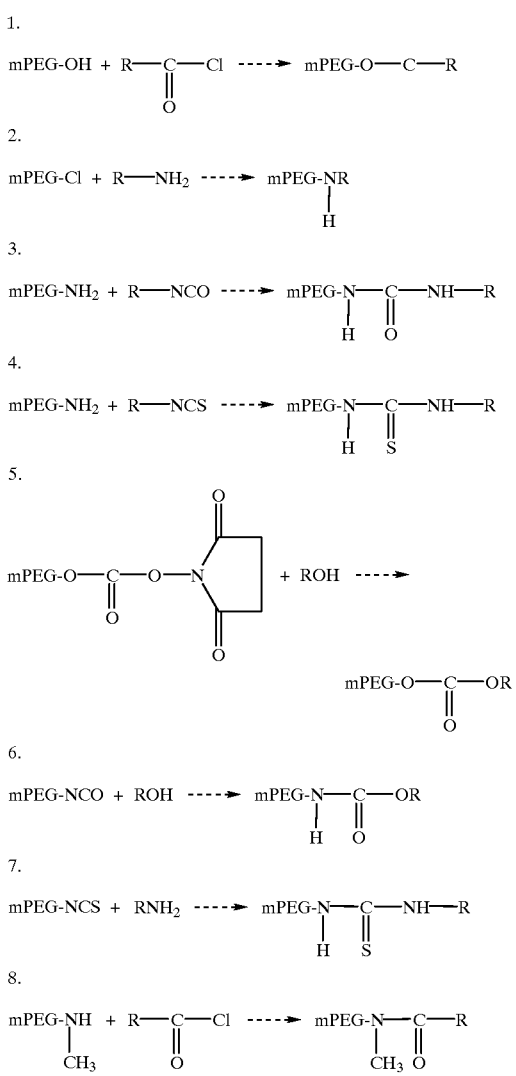

In the above mechanisms, mPEG represents a methoxypolyethylene glycol or a methoxypolypropylene glycol having a molecular weight of from about 1.000 to about 40,000, and R is a $C_8$–$C_{24}$ alkyl group. The other variant species of the polymer can be prepared by those skilled in the art in an analogous manner. It is to be understood that the mPEG derivatives are shown above for purpose of illustration and that the alternative polymers described above can also be converted into the inventive compounds using suitable techniques.

In the practice of the present invention, the water-soluble complex is prepared by combining the desired water-insoluble compound such as a medicinal agent or drug with the polymer in an organic solvent in which both are soluble and then removing the solvent. Suitable water-insoluble compounds include essentially any compound which can benefit from increased water solubility. It should be capable of forming a non-covalent complex with the water-soluble polymeric compound. For the purposes of this invention water-insoluble compounds are those having solubilirty in water of less than 10 mg/ml and preferably less than 1 mg/ml. Examples of suitable medicinal agents non-exclusively include tacrine, Amphotericin-B, campthothecin, free base forms of antibiotics, cyclosporin-A, anti-arrhythmic, anti-inflammatory, anti-anxiety and anti-psychotic agents, etc. Preferred aspects of the invention include complexes of Amphotericin-B or tacrine with the polymers described herein.

Suitable organic solvents non-exclusively include alcohols, ketones, ethers, esters, dimethylformamide and mixtures thereof. Alcohols, however, particularly ethanol, are most preferred. The mixing temperature should be below the decomposition temperature of the components, and is preferably from about 4° C. to about 115° C., most preferably about 25 to 60° C.

The water-soluble polymer containing the terminal hydrophobic group is preferably combined with the water-insoluble compound is a mole ratio of generally from about 1:1 to about 4:1, preferably from about 1:1 to about 2:1 and most preferably 1:1. The reaction is conducted in an inert solvent which is present in that amount sufficient to form a homogenous solution of the components. Thereafter, the solvent is removed such as by evaporating or vacuum.

When the water-insoluble compound is a bio-effecting substance or drug, the formed complex retains at least a portion of the bioactivity of the drug prior to complexing. For purposes of the present invention, the term "bio-effecting substance" means a substance capable of having a biologically determinable effect in mammals. "Portion of the activity" shall be understood to mean that at least some therapeutic effectiveness is maintained.

Another aspect of the present invention provides methods of treatment for various medical conditions in mammals. The methods include administering an effective amount of the drug-containing complex which has been prepared as described herein to a mammal in need of such treatment. The complexes are useful for, among other things, treating infections, as in the case of Amphotericin-B complexes, neurological conditions, as in the case of tacrine complexes, neoplastic disease, reducing tumor burden, preventing metastasis of neoplasms and preventing recurrences of tumor/neoplastic growths, in the case of anti-neoplastic agent complexes. The amount of complex used in the treatment methods is generally that amount which effectively achieves the desired therapeutic result in mammals. Naturally, the dosages of the various complexes will vary depending upon the intended use and medicinal agent selected. Those skilled in the art will determine the optimal dosing of the conjugate selected based on clinical experience and the treatment indications.

The complexes of the present invention can be included in one or more suitable pharmaceutical compositions for administration to mammals. The pharmaceutical compositions may be in the form of a solution, suspension, tablet capsule or the like, prepared according to methods well known in the art. It is also contemplated that administration of such compositions may be by the oral and/or parenteral routes depending upon the needs of the artisan. In preferred aspects, the complexes are administered as aqueous solutions.

In the case of Amphotericin-B, it has been surprisingly found that the complexes and methods of the present invention provide a means for increasing its water-solubility and reducing its toxicity to erythrocytes.

In this aspect of the invention, the amount of Amphotericin-B polymeric complex administered will be based on the amount of Amphotericin contained therein. For example, the amount administered will range from about 0.1 to about 10 mg/kg/day and preferably from about 0.2 to about 3 mg/kg/day.

The following non-limiting examples serve to illustrate the invention but are not meant in any way to restrict the effective scope of the invention.

EXAMPLE 1

Preparation of Succinimidylcarbonate-Polyethylene Glycol (mSCPEG)

Methoxypolyethylene glycol of molecular weight 5,000 (Union Carbide, 60 g 12 mmol) was dissolved in toluene/dichloromethane (3:1 200 ml) and treated with a toluene solution of phosgene (20 mg, 57 mmol) overnight. The solution was evaporated to dryness and the remainder of phosgene was removed under vacuum. The residue was redissolved in toluene/dichloromethane (2.1, 150 ml) and treated with solid N-hydroxysuccinimide (2:1 g, 18 mmol) followed by triethylamine (1.7 ml, 12 mmol). After 3 hours, the solution was filtered and evaporated to dryness. The residue was dissolved in warm (50° C.) ethyl acetate (600 ml), filtered from trace insolubles and cooled to facilitate precipitation of the polymer. The product was collected by filtration and then recrystallized once more from ethylacetate. The product as dried in vacuo over $P_2O_5$. The yield was 52.5 g (85% of theoretical). To determine the active carbonate content of the product, samples of the polymer were reacted with a measured amount of benzylamine in dichloromethane and the excess of amine was titrated with perchloric acid in dioxane. These titrations indicated that 1 g of the product contained 1.97 $\times 10^{-4}$ mole of active carbonate (101% of theoretical content). I.R. (film on NaCl, $cm^{-1}$) characteristic bands at: 1812 and 1789 (both C=O, succinimide); 1742 (C=O, carbonate); 1114 ($CH_2OCH_2$). $C^{13}$-NMR ($CDCl_3$): delta 168.5 ($CH_2C$=O); 151.3 (O—$CO_2$); 71.9 ($CH_3OCH_2$); 70.2 (PEG); 68.7 ($CH_2CH_2OCO_2$); ($CH_3HC_2OCO_2$); 68.0 ($CH_2CH_2OCO_2$); 58.9 ($CH_3O$); 25.2 ($CH_3C$=O) ppm.

EXAMPLE 2

Preparation of Octadecyl Carbamate of Methoxypolyethylene Glycol

Octadecyl amine (3.25 g) 0.012 moles is added to a solution of mSCPEG (Ex. 1) (50.4 g, 0.008 mol) in dichloromethane (200 ml) and the contents are stirred for one hour. The solvent is evaporated and the solid obtained is recrystallized from 2-propanol and ethyl ether to give the octadecyl carbamate of methoxypolyethylene glycol. $C^{13}$ NMR confirms the analysis.

EXAMPLE 3

Preparation of Octyl Carbamate of Methoxypolyethylene Glycol

The procedure of Example 2 was repeated except that 0.012 moles of octyl amine was used instead of octadecyl amine. Octyl carbamate of methoxypolyethylene glycol resulted.

EXAMPLE 4

Preparation of n-Octylamino-m-PEG

A mixture of 25 g (5.0 mmoles) of m-PEG-Cl and 6.5 g (50 mmoles) of n-octylamine in 100 ml of water is placed in a 250 ml polypropylene bottle. This sealed bottle is kept in a water bath at 60° C. for 48 hours with occasional agitation, followed by cooling to room temperature and removal of the solvent by distillation in vacuo. The product is purified by recrystallization from 2-propanol.

EXAMPLE 5

Preparation of Norbornylamino-m-PEG

A mixture of 25 g (5.0 mmoles) of m-PEG-Cl and 5.6 g (50 mmoles) of 2-aminonorbornane (available from Aldrich Chemical) in 100 ml of water is placed in a 250 ml polypropylene bottle. This sealed bottle is kept in a water bath at 60° C. for 48 hours with occasional agitation, followed by cooling to room temperature and removal of the solvent by distillation in vacuo. The product is purified by recrystallization from 1-propanol.

EXAMPLE, 6

Preparation of Norbornyl-m-PEG-Amide

A solution of 20 g (4.0 mmoles) of m-PEG acid, 0.7 g (6.3 mmoles) of 2-aminonorbornane (available from Aldrich Chemical), 0.8 g (6.3 mmoles) of diisopropylcarbodiimide and 0.8 g (6.3 mmoles) of dimethylaminopyridine in 100 ml of dichloromethane is stirred for 18 hours at room temperature. Removal of the solvent in vacuo, followed by recrystallization from 2-propanol yielded the mPEG amide.

EXAMPLE 7

Preparation of Tacrine-Octadecyl Carbamate of mPEG Complex

A solution of tacrine (80 mg, 0.34 mmol.) in methanol (3 ml) is added to a solution of the octadecylcarbamate of methoxypolyethylene glycol, (1.99 g, 0.34 mmol) in methanol (80 ml). The contents are stirred overnight. The reaction is worked out by removing the solvent and the solid obtained is dissolved in water (80 ml). This water solution is passed through a 0.4 micron filter to remove particulates and lyophilized to give a white powder. This product (2.07 g) exhibits a different HPLC retention time than the tacrine starting material. Tacrine has a retention time of 13 minutes on a $C_8$ reverse phase column using methanol as mobile phase whereas the product has a retention time of 26 minutes. $C_{13}$ NMR and $^1$H NMR of this product in methanol indicates resonances corresponding to tacrine as well as the octadecyl carbamate of methoxy polyethylene glycol. Stability of this compound was determined by dissolving small amounts in water, pH 7.8 phosphate buffer and methanol. All solutions remain clear for at least three months.

| COMPOUND | HPLC RT (MIN) | WATER SOLUBILITY | STABILITY |
|---|---|---|---|
| Tacrine in methanol | 13 | Insoluble | n/a |
| Tacrine + octadecyl carbamate of methoxypoly-ethylene-glycol in methanol | 26 | Soluble (100 mg/ml) | Stable in deionized water, pH 7.26 |

| COMPOUND | HPLC RT (MIN) | WATER SOLUBILITY | STABILITY |
|---|---|---|---|
| | | | phosphate buffer and methanol for 7 weeks. |

EXAMPLE 8

A solution of tacrine (100 mg, 0.43 mmol) is added to a solution of the octylcarbamate of methoxypolyethylene glycol, (1.99 g, 0.34 mmol) in methanol (120 ml). The contents are stirred overnight and the reaction is worked as in Example 7. The product obtained is stable in water for 12 hours and in a pH 7.8 phosphate buffer is found to be stable for at least three months.

EXAMPLE 9 (COMPARATIVE)

A solution of tacrine (100 mg, 0.43 mmol) in methanol (3 ml) is added to a solution of propylcarbamate of methoxypolyethylene glycol), 2.3 g, 0.45 mmol) in methanol (120 ml). The propyl carbamate of mPEG was prepared in a manner similar to that set forth in Examples 2–3. The contents are stirred overnight. Methanol is removed and 100 ml of water is added to the solid obtained. The solution is not homogenous as in Examples 7 and 8. The solid is insoluble in water and indicates that the desired complex for making tacrine water-soluble is not formed.

EXAMPLE 10 (COMPARATIVE)

Solid tacrine (100 mg, 0.43 mmol) is added to a solution of the octadecylcarbamate of methoxypolyethylene glycol, (2.3 g, 0.45 mmol) in water (100 ml) and the contents stirred overnight. The tacrine remains insoluble in water indicating that an organic solvent, such as methanol, is needed for complex formation.

EXAMPLE 11 (COMPARATIVE)

A solution of methoxypolyethylene glycol, (2.2 g., 0.43 mmol) in methanol (90 ml) is added to a solution of tacrine (100 mg, 0.43 mmol) in methanol (3 ml). The contents are stirred overnight. Methanol is removed and water (150 ml) is added to dissolve the solid. Approximately 100 mg of the solid remains insoluble indicating that methylpolyethylene glycol-OH is not able to form the inventive complexes whereas when a sufficiently long, i.e., $C_8$ or greater hydrophobic chain is attached to this molecule the inventive complexes readily form.

EXAMPLE 12

Determination of Cholinesterase Activity

The tacrine-PEG compounds from Example 7 are tested for their ability to inhibit eel or human red blood cell AChE activity. The modified radiometric AChE assay of Johnson and Russell, *Anal Biochem.*, (1975) 64, 229 and Emmerling & Sabkowicz, *Hearing Res.*, (1988) 32, 137 is used for the determination of $IC_{50}$ values with ACh chloride, (acetyl-$^3$H) from New England Nuclear (specific activity of 90 mCi/mmole) as substrate. The concentration of inhibitor producing 50% inhibition of AChE activity ($IC_{50}$) is determined graphically using data derived from triplicate determinations of enzyme inhibition by at least six different inhibitory concentrations ranging from 1 nM to 100 uM Butyrylcholinesterase (BuChE) activity is determined by the microplate colorimetric Ellman assay using 1 mM butyrylthiochloine as substrate. The assays were done in triplicate and read using a Molecular Devices Thermomax microplate reader set at 405 nm. Using tacrine HCl, the determined $IC_{50}$ value is observed to be 30 nM. For the complex formed according to the procedure of Example 7 above, i.e., with the octadecyl carbamate of methoxypolyethylene glycol (5000) and tacrine, the determined $IC_{50}$ value is observed to be 23.3 nM. Therefore, these are determined to be essentially equipotent.

EXAMPLE 13

Amphotericin-B is a water-insoluble antifungal agent which has become the mainstay of therapy for candida albicans infections. In order to make it water-soluble, an equimolar amount of Amphotericin-B and the Octadecyl carbamate of methoxypolyethylene glycol are dissolved in a dimethylformamide/ethanol mixture and stirred for 18 hours at room temperature and the solvent evaporated. The solid obtained is redissolved in water and passed through a 0.4 micron filter to remove the particulates. The resulting clear, yellow solution is frozen and lyophilized to give a yellow powder which is water-soluble. There is no difference in retention time on reverse-phase HPLC between the starting material and product. $^1$H NMR behavior is similar to the individual components. The stability of the product is determined by dissolving in deionized water and pH 7.26 phosphate buffer. Solid Amphotericin-B precipitates from the buffer solution in two weeks, whereas the water solution remains clear for at least 7 weeks when the experiment is stopped.

| COMPOUND | HPLC RT (MIN) | WATER SOLUBILITY | STABILITY |
|---|---|---|---|
| Amphotericin-B | 8.13 | Insoluble | n/a |
| Amphotericin-B plus octadecyl carbamate of ethoxy-polyethylene-glycol | 8.13 | Soluble (8 mg/ml) | Stable up to 2 weeks in pH 7.26 phosphate buffer and 7 weeks in deionized water |

EXAMPLE 14

In this Example, the anti-fungal and hemolytic activities of the Amphotericin-B polymer complex of Example 13 were compared to those of Amphotericin-B.

To test anti-fungal activity, *Candida albicans* ATCC 32089 was grown in 2 ml of YPD broth (Yeast extract-Peptone-Dextrose broth; page 1079 in Atlas, R.M. and L.C. Parks (ed), *Handbook of Microbiological Media* 1993, CRC Press) overnight at 37° C. in a shaker. The overnight culture was diluted with an equal volume of fresh YPD broth and incubated for 2 more hours. 50 µl of this inoculum culture was added to each of a series of tubes containing 5 ml of YPD broth and various concentrations of Amphotericin-B ("Ampho;" added from a stock solution of 1 mM in DMSO) or Amphotericin-B polymer complex ("PegAmpho;" added from a stock solution of 1 mM in sterile distilled water). Tubes were incubated at 37° C. with shaking (200 rpm) for 8 hours, and the extent of growth was then determined by measuring the optical density of the tube cultures at a wavelength of 600 nm. As can be seen from FIG. 1, the complexation of the drug with the polymeric compositions of the present invention does not detract from antifungal activity.

Figure 2:
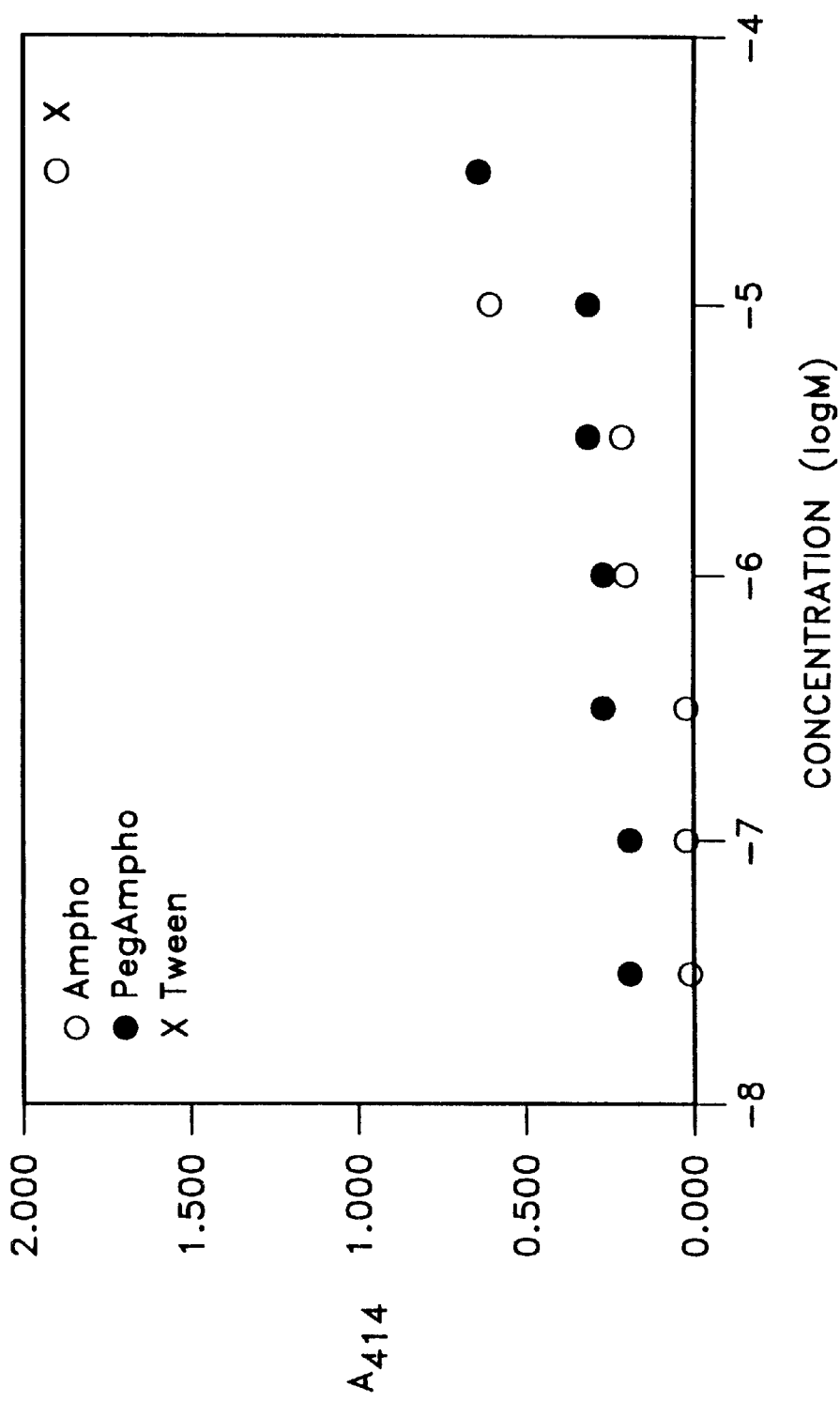
FIG. 2 is a graphical representation of the effect of amphotericin and polyethylene glycol conjugated amphotericin in accordance with the present invention on hemolysis.

The ability of the complexes to reduce the toxicity of Amphotericin-B was shown using the erythrocyte hemolysis toxicity assay as described by Forster et al., *J. Pharm. Pharmacol.*, 40: 325–328 (1988). A sample of fresh human blood was added at a 1/50 dilution to each of a series of tubes containing 10 mM phosphate buffered saline, pH 7, and various concentrations of Amphotericin-B ("Ampho;" added from a stock solution of 1 mM in DMSO) or Amphotericin-B polymer complex ("PegAmpho;" added from a stock solution of 1 mM in sterile distilled water). The detergent tween at a concentration of 1% was used in the control to lyse 100% of the erythrocytes. The tubes were incubated at 37 C. for 4 hours and then centrifuged al 12,000 xg for 5 minutes. Optical density of each supernatant was measured at a wavelength of 414 nm. As can be seen from FIG. 2, the complexes of the present invention caused less toxicity (i.e., hemolysis) than did Amphotericin-B at concentrations of $10^{-5}$ M or greater.

The results of this Example demonstrate that the Amphotericin-B polymer complexes of the present invention maintain anti-fungal activity but have reduced toxicity (i.e., hemolytic activity).

What is claimed is:

1. A water-soluble, polymeric compound of the formula:

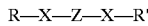

wherein:

R is a $C_6$–$C_{30}$ alkyl, cycloakyl, bicycloalkyl or olefin group;

X is independently selected from the group consisting of: sulfur,

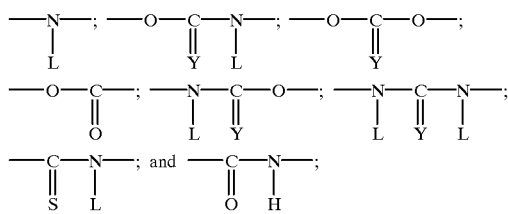

wherein L is H or a $C_{1-4}$ alkyl; and Y is O or S;

Z is a polyalkylene oxide homopolymer or copolymer residue; and

R' is a $C_{1-24}$ alkyl.

2. The compound of claim 1, wherein the compound has a molecular weight of from about 1,000 to about 40,000.

3. The compound of claim 1, wherein Z is a polyethylene glycol residue.

4. The compound of claim 1, wherein Z has a molecular weight of from about 2,000 to about 12,000.

5. The compound of claim 1, wherein Z has a molecular weight of from about 2000 to about 5000.

6. The compound of claim 1, wherein R is a $C_{18}$ alkyl group and R' is methyl.

7. The compound of claim 1, wherein at least one X is

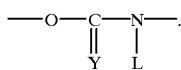

8. A method of preparing a water-soluble complex comprising:
   a) contacting a substantially water insoluble compound with a water soluble compound, polymeric compound having the structure:

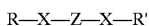

wherein:
   R is a $C_6$–$C_{30}$ alkyl, cycloakyl, bicycloalkyl or olefin group;
   X is independently selected from the group consisting of: sulfur,

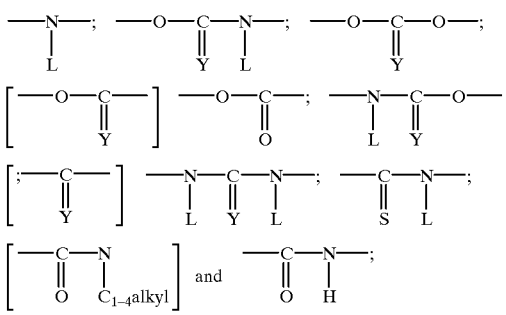

where L is H or a $C_{1-4}$ alkyl; and Y is O or S;
   Z is a polyalkylene oxide homopolymer or copolymer residue; and
   R' is a $C_{1-24}$ alkyl
   which compound has a molecular weight of from about 1,000 to about 40,000; and
   b) separating the complex from the organic solvent.

9. The method of claim 8, further comprising the step of mixing the complex with an aqueous solution.

10. A method of administering Amphotericin-B to a mammal in need thereof, comprising preparing a water-soluble, non-covalent complex of Amphotericin-B with a water soluble polymer having the formula:

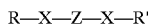

wherein:
    R is a $C_6$–$C_{30}$ alkyl, cycloakyl, bicycloalkyl or olefin group;
    X is independently selected from the group consisting of: sulfur,

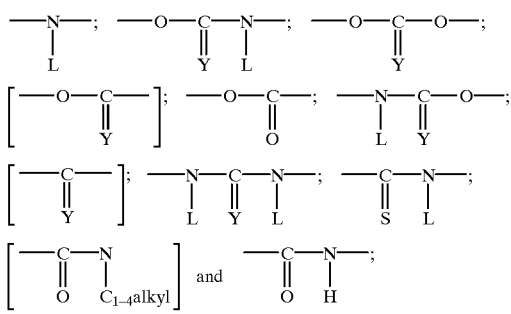

where L is H or a $C_{1-4}$ alkyl; and Y is O or S;
    Z is a polyalkylene oxide homopolymer or copolymer residue; and
    R' is a $C_{1-24}$ alkyl; mixing the complex with water to form a solution, and administering said solution to a mammal in need thereof.

11. The method of claim 10, wherein said Amphotericin-B is administered in an amount of from about 0.2 mg/kg/day to about 3.0 mg/kg/day.

* * * * *